United States Patent
Honing et al.

(10) Patent No.: US 8,440,624 B2
(45) Date of Patent: May 14, 2013

(54) PEPTIDE WHITENING AGENTS AND COSMETIC COMPOSITIONS COMPRISING THE SAME

(75) Inventors: Stefan Honing, Euskirchem (DE); Gaelle Saintigny, Paris (FR)

(73) Assignee: Chanel Parfums Beaute, Neuilly-sur-Seine (FR)

( * ) Notice: Subject to any disclaimer, the term of this patent is extended or adjusted under 35 U.S.C. 154(b) by 570 days.

(21) Appl. No.: 12/668,773

(22) PCT Filed: Jun. 16, 2008

(86) PCT No.: PCT/EP2008/057558
§ 371 (c)(1),
(2), (4) Date: Jan. 12, 2010

(87) PCT Pub. No.: WO2009/010356
PCT Pub. Date: Jan. 22, 2009

(65) Prior Publication Data
US 2010/0190721 A1 Jul. 29, 2010

Related U.S. Application Data

(60) Provisional application No. 60/929,818, filed on Jul. 13, 2007.

(51) Int. Cl.
*A61K 38/08* (2006.01)
*C07K 7/06* (2006.01)

(52) U.S. Cl.
USPC ........................................ 514/18.8; 530/328

(58) Field of Classification Search .................. None
See application file for complete search history.

(56) References Cited

FOREIGN PATENT DOCUMENTS

| JP | 06321757 A | 11/1994 |
|---|---|---|
| WO | 95/34280 A | 12/1995 |
| WO | 97/35998 A | 10/1997 |
| WO | 2005/048968 A | 6/2005 |

OTHER PUBLICATIONS

Park Hee-Young et al: "Topical application of a protein kinase C inhibitor reduces skin and hair pigmentation." The Journal of Investigative Dermatology Jan. 2004, vol. 122, No. 1, Jan. 2004, pp. 159-166.
Setaluri V: "Sorting and targeting of melanosomal membrane proteins: signals, pathways, and mechanisms." Pigment Cell Research 1 Sponsored by The European Society for Pigment Cell Research and The International Pigment Cell Society Jun. 2000, vol. 13, No. 3, Jun. 2000, pp. 128-134.
Honing S et al: "A di-leucine-based motif in the cytoplasmic tail of LIMP-II and tyrosinase mediates. selective binding of AP-3." The EMBO Journal, vol. 17, No. 5, Aug. 10, 1998, pp. 1304-1314.
Theos Alexander C et al: "Functions of adaptor protein (AP)-3 and AP-1 in tyrosinase sorting from endosomes to melanosomes." Molecular Biology of the Cell Nov. 2005, vol. 16, No. 11, Nov. 2005, pp. 5356-5372.
Wang Ning et al: "Tyrosinase maturation through the mammalian secretory pathway: bringing color to life." Pigment Cell Research 1 Sponsored by The European Society for Pigment Cell Research and The International Pigment Cell Society Feb. 2006, vol. 19, No. 1, Feb. 2006, pp. 3-18.
International Search Report in Corresponding Application PCT/EP2008/057558 Dated Nov. 11, 2008.

*Primary Examiner* — Robert A Wax
*Assistant Examiner* — Jessica Worsham
(74) *Attorney, Agent, or Firm* — Young & Thompson (57) ABSTRACT

The present invention relates to novel peptide compounds having the following formula $[R_1R_2N-CH(Ra)-CO]_a$-$(AA_1)_m$-$(AA_2)_b$-$X_1$-$X_2$-$X_3$-$Y_1$-$Y_2$-$Y_3$-$X_4$-$(AA_3)_n$-$[NH-CH(Rb)-COOR_3]_c$. It also pertains to cosmetic and dermatological compositions comprising one or more of these peptide compounds and to their uses in the cosmetic whitening of human skin and for the manufacture of a dermatological preparation intended to depigment human skin.

8 Claims, 4 Drawing Sheets

```
                        SEQUENCE LISTING

<160> NUMBER OF SEQ ID NOS: 11

<210> SEQ ID NO 1
<211> LENGTH: 9
<212> TYPE: PRT
<213> ORGANISM: Artificial
<220> FEATURE:
<223> OTHER INFORMATION: WHITENING AGENT

<400> SEQUENCE: 1

Asp Glu Arg Gln Pro Leu Leu Val Glu
1               5

<210> SEQ ID NO 2
<211> LENGTH: 9
<212> TYPE: PRT
<213> ORGANISM: Artificial
<220> FEATURE:
<223> OTHER INFORMATION: WHITENING AGENT
```

```
<400> SEQUENCE: 2

Glu Glu Arg Gln Pro Met Leu Leu Asp
1               5

<210> SEQ ID NO 3
<211> LENGTH: 9
<212> TYPE: PRT
<213> ORGANISM: Artificial
<220> FEATURE:
<223> OTHER INFORMATION: WHITENING AGENT

<400> SEQUENCE: 3

Ala Glu Asp Glu Pro Leu Leu Met Glu
1               5

<210> SEQ ID NO 4
<211> LENGTH: 9
<212> TYPE: PRT
<213> ORGANISM: Artificial
<220> FEATURE:
<223> OTHER INFORMATION: WHITENING AGENT

<400> SEQUENCE: 4

Ala Glu Asp Glu Pro Leu Leu Val Asp
1               5

<210> SEQ ID NO 5
<211> LENGTH: 10
<212> TYPE: PRT
<213> ORGANISM: Artificial
<220> FEATURE:
<223> OTHER INFORMATION: WHITENING AGENT

<400> SEQUENCE: 5

Met Val Glu Glu Asn Pro Ile Leu Met Glu
1               5                   10

<210> SEQ ID NO 6
<211> LENGTH: 30
<212> TYPE: PRT
<213> ORGANISM: Artificial
<220> FEATURE:
<223> OTHER INFORMATION: Tyrosinase tail peptide

<400> SEQUENCE: 6

Cys Arg His Lys Arg Lys Gln Leu Pro Glu Glu Lys Gln Pro Leu Leu
1               5                   10                  15

Met Glu Lys Glu Asp Tyr His Ser Leu Tyr Gln Ser His Leu
            20                  25                  30

<210> SEQ ID NO 7
<211> LENGTH: 11
<212> TYPE: PRT
<213> ORGANISM: Artificial
<220> FEATURE:
<223> OTHER INFORMATION: TGN 38 fragment

<400> SEQUENCE: 7

Cys Arg Pro Lys Ala Ser Asp Tyr Gln Arg Leu
1               5                   10

<210> SEQ ID NO 8
<211> LENGTH: 12
<212> TYPE: PRT
<213> ORGANISM: Artificial
<220> FEATURE:
```

-continued

<223> OTHER INFORMATION: lamp-1 fragment

<400> SEQUENCE: 8

Cys Arg Lys Arg Ser His Ala Gly Tyr Gln Thr Ile
1               5                   10

<210> SEQ ID NO 9
<211> LENGTH: 10
<212> TYPE: PRT
<213> ORGANISM: Artificial
<220> FEATURE:
<223> OTHER INFORMATION: control

<400> SEQUENCE: 9

Arg Pro Lys Ala Ser Asp Tyr Gln Arg Leu
1               5                   10

<210> SEQ ID NO 10
<211> LENGTH: 11
<212> TYPE: PRT
<213> ORGANISM: Artificial
<220> FEATURE:
<223> OTHER INFORMATION: control

<400> SEQUENCE: 10

Arg Lys Arg Ser His Ala Gly Tyr Gln Thr Ile
1               5                   10

<210> SEQ ID NO 11
<211> LENGTH: 9
<212> TYPE: PRT
<213> ORGANISM: Artificial
<220> FEATURE:
<223> OTHER INFORMATION: control

<400> SEQUENCE: 11

Glu Glu Lys Gln Pro Leu Leu Met Glu
1               5

PEPTIDE WHITENING AGENTS AND COSMETIC COMPOSITIONS COMPRISING THE SAME

FIELD OF THE INVENTION

The present invention relates to novel peptide compounds that are specifically recognized by heterotetrameric adaptor protein complexes (AP) and more specifically by AP3 and AP2 adaptor complexes having a key role in the transport of tyrosinase and thus in melanogenesis. It also pertains to cosmetic compositions comprising these compounds, to a cosmetic whitening method comprising the topical application of such compositions onto human skin and to the use of this composition for manufacturing a dermatological preparation intended to depigment human skin.

BACKGROUND OF THE INVENTION

Extensive research has been conducted over the past years to extract or synthesize new whitening agents to be used in cosmetic and dermatological compositions in order to alleviate skin pigmentation defects such as senile lentigo or chloasma or to satisfy consumers who are eager to have the lightest possible complexion.

Various whitening agents acting on melanogenesis have been proposed to this end. Among them, however, some only show a slight melanogenesis-inhibiting effect failing to provide a sufficient whitening effect, while others, which are more effective, have proven not to be free of side effects on account of their toxicity to human skin cells, rendering their use quite hazardous in cosmetics. This toxicity arises from the fact that they interfere with fundamental mechanisms of melanogenesis, by killing cells and thus forcing the skin to eliminate them while producing toxins.

For instance, hydroquinone is a compound which is particularly irritant and cytotoxic to melanocytes, and whose total or partial replacement has been contemplated by many investigators. In order to overcome the drawbacks mentioned above, it has been suggested, for example, to use derivatives of active compounds such as fatty acid esters or glycosyl ethers of hydroquinone as depigmenting agents. Unfortunately, although more photostable and less toxic than hydroquinone, these derivatives, such as arbutin, are less active than hydroquinone to improve the aspect of pigmentary defects.

Other substances have been sought which are not involved in the mechanism of melanogenesis, but which act upstream on tyrosinase by preventing its activation, and are consequently much less toxic. Tyrosinase is regarded as the key enzyme in melanin synthesis, and catalyses the first two reactions, the hydroxylation of L-tyrosine to 3,4-dihydrophenylalanine (DOPA) and the oxidation of DOPA to DOPAquinone. Kojic acid is commonly used as a tyrosinase-activation inhibitor by complexing the copper present in the active site of the enzyme. Unfortunately, this compound can give rise to allergic reactions (Nakagawa et al, in Contact Dermatitis, 1995). In addition, this compound is unstable in solution, which somewhat complicates the manufacture of a composition containing it.

Other whitening agents acting on tyrosinase activity are plant extracts, the efficacy of which is not always satisfactory. A possible explanation for the limited efficacy of these known whitening agents is that they lack proper access to tyrosinase inside the melanosomes. The melanosomal membrane is indeed a very impervious structure which protects the cell from very toxic metabolites (quinones) generated during melanogenesis.

Another approach to inhibit skin melanogenesis is to act on the process of tyrosinase maturation. Tunicamycin has for instance been proposed to this end, since this compound disturbs tyrosinase glycosylation which is necessary for its maturation and for its migration from the Golgi to the melanosomes. However, the inhibition of glycosylation is unspecific and associated with a number of side effects rendering the cosmetic use of this compound unsuitable. Similarly, other agents have been proposed which are able to modify the conformation of tyrosinase so as to lower its stability and direct it to the degradation pathways (ER-associated degradation or through the endosomal/lysosomal system). However, the major drawback of this approach is that it may also interfere with the maturation of other proteins and thus alter a number of biological mechanisms other than melanogenesis. Again, this is not conceivable for a cosmetic product.

SUMMARY OF THE INVENTION

Thus, there is still a need for an agent for bleaching human skin which acts as effectively as, or even better than known agents, but which does not exhibit their drawbacks, i.e. which is non-irritant, non-toxic and/or non-allergenic to the skin and which is stable in a composition.

To satisfy this need, this invention uses an alternative way for inhibiting the pigmentation process which is not only safer but also very effective since it acts upstream of melanosome formation, well before the formation of its membrane. More specifically, the novel compounds of this invention have been conceived so as to interfere with the intracellular transport of tyrosinase to melanosomes. The problem of accessibility of the active agents to their biological target is thus overcome. Moreover, these compounds have a rather specific activity against melanogenesis, since they inhibit and/or reduce tyrosinase transport from the TGN (Trans Golgi Network) to melanosomes. They are thus not likely to interfere with any other biological process, which makes them well suited for a cosmetic application.

Melanosomes differ from lysosomes by the presence of enzymes involved in pigment synthesis, as for example tyrosinase. Tyrosinase is only active in a maturing melanosome, but not in other organelles of its biosynthetic pathway. Thus, the approach chosen by the inventors is to use short peptides to block the binding of tyrosinase to the cytosolic heterotetrameric adaptor complexes (AP) and specifically to AP-2 and AP-3, which are a key component of the intracellular sorting machinery (Honing et al., EMBO J., 17, no 5, 1304-1314, 1998 and Honing et al., Mol. Cell., 2005, 18, 519-531). One of the key function of AP complexes is to bind membrane proteins such as tyrosinase via short peptide sequences located in their intracellular tail. By binding cytoplasmic sorting signals on cargo proteins, AP complexes recruit cargo to patches on donor membranes that bud to form vesicles or tubules intended to fuse with target membranes (Bonifacio and Traub, Annu. Rev. Biochem., 72, 395-447, 2003).

More specifically, it has been demonstrated that tyrosinase has a high affinity interaction with AP-3. AP-3 is an adaptor complex composed of the four subunits δ-adaptin, β3A-adaptin, the medium chain μ3A and the small chain σ3A. It was demonstrated (DELL'ANGELICA E C et al., EMBO J., 16, 917-928, 1997) that the μ3 chain can interact with tyrosine-based sorting signals and that AP-3 binds dileucine-based signals, which are involved in the transport of tyrosinase to melanosomes. Preventing the binding between AP3 and tyrosinase should thus inhibit the incorporation of tyrosinase in the formation of the melanosomes and thus melanogenesis.

The novel compounds of this invention are peptide compounds which, to the best of the inventors's knowledge, have never been described or used before in cosmetics.

The present invention thus pertains to a compound having the following formula (I):

$$[R_1R_2N-CH(Ra)-CO]_a\text{-}(AA_1)_m\text{-}(AA_2)_b\text{-}X_1\text{-}X_2\text{-}X_3\text{-}Y_1\text{-}Y_2\text{-}Y_3\text{-}X_4\text{-}(AA_3)_n\text{-}[NH-CH(Rb)-COOR_3]_c \quad (I)$$

wherein:

$R_1$, $R_2$, $R_3$ each independently represent:
H,
a $C_2$-$C_{22}$ optionally hydroxylated and/or sulphured linear hydrocarbon group which may be saturated or unsaturated,
a $C_3$-$C_{22}$ optionally hydroxylated and/or sulphured branched or cyclic hydrocarbon group which may be saturated or unsaturated, or
a biotin group,
wherein at least one of $R_1$ and $R_2$ may alternatively be a protective group or a blocking group Ra and Rb each independently represent: H; a $C_1$-$C_4$ linear alkyl group; or a $C_3$-$C_4$ branched alkyl group, each alkyl group optionally being substituted by one or more substituents selected from the group consisting of: OH, SH, COOH, $CONH_2$, $NH_2$—S—$CH_3$, NH—C(NH)—$NH_2$ or by a cyclic or heterocyclic aromatic group, $X_1$, $X_2$ and $X_4$ each independently represent a polar amino acid group, $X_3$ is a small, preferably uncharged, amino acid group, $Y_1$, $Y_2$ and $Y_3$ each independently represents a hydrophobic amino acid group with the proviso that at least one of $Y_1$ and $Y_2$ is leucine or isoleucine, $AA_1$, $AA_2$ and $AA_3$ independently designate amino acid groups, wherein the $AA_1$ and $AA_3$ amino acid groups, respectively, may be the same or different when m and n are more than 1, m and n independently represent an integer ranging from 0 to 10,
a, b and c are independently 0 or 1,
wherein all the amino acid groups may independently be in a L, D or DL configuration,
with the proviso that when $X_1$ is arginine (R) or lysine (K), then $Y_2$ is different from methionine (M).

By "protecting or blocking group", is in intended to mean any chemical moiety capable of preventing reactivity of the amino groups in the peptide, for instance when undergoing a reaction at a carboxyl group of the molecule. Exemplary protective groups include, but are not limited to, tBoc (tert-butyloxycarbonyl), Z (benzoylcarbonyl), Fmoc (fluorenylmethyloxycarbonyl) and Alloc (allyloxycarbonyl) groups. These and additional protecting and blocking groups useful in peptide synthesis are well known in the art.

Moreover, the term "hydrocarbon group" is intended to mean any group having carbon and hydrogen atoms in its structure, for instance in its main chain. This hydrocarbon group may also include other atoms, such as oxygen and/or nitrogen atoms. Non limiting examples of $R_1$ and/or $R_2$ hydrocarbon groups are alkyl carbonyl and alkenyl carbonyl groups. Among them, alkyl carbonyl groups having from 6 to 20 carbon atoms, such as a palmitoyl group, are preferred. Non limiting examples of $R_3$ hydrocarbon groups are alkyl and alkenyl groups comprising from 1 to 20 carbon atoms.

Among polar amino acid groups, mention can be made of those selected from the group consisting of: asparagine (N), serine (S), cysteine (C), glutamine (Q), aspartic acid (D), glutamic acid (E), threonine (T), lysine (K), arginine (R), histidine (H), tyrosine (Y) and tryptophan (W).

Among small amino acid groups, mention can be made of those selected from the group consisting of: proline (P), asparagine (N), aspartic acid (D), threonine (T), valine (V), cysteine (C), alanine (A), serine (S) and glycine (G).

Among hydrophobic amino acid groups, mention can be made of those selected from the group consisting of: alanine (A), glycine (G), cysteine (C), threonine (T), valine (V), isoleucine (I), leucine (L), lysine (K), methionine (M), histidine (H), tyrosine (Y), tryptophan (W) and phenylalanine (F).

It should be noted that the orientation of the amino- and c-terminus of the peptide is irrelevant to the inhibitory effect of the above compounds.

The groups between brackets in Formula (I) may advantageously be present (a and/or c equal to 1) so as to facilitate solubility, membrane penetration and/or detection of the compounds of this invention or simply for protecting the peptide against degradation. They can also be useful for strengthening the binding of these peptides to the AP-2 and/or AP-3 adaptor complexes.

In the above formula (I), it is preferred that:
$AA_2$ and/or $X_4$ designates a polar amino acid group which is preferably charged and more preferably negatively charged, and/or
$X_1$ is a charged polar amino acid group, and/or
$X_3$ is proline (P), and/or
$Y_1$ and/or $Y_2$ and/or $Y_3$ is an aliphatic amino acid group, such as valine (V), isoleucine (I) or leucine (L),
with the proviso that when $X_1$ is arginine (R) or lysine (K), then $Y_3$ is different from methionine (M).

According to a preferred embodiment of this invention:
b=1 and $AA_2$, is glutamic acid (E),
$X_1$ is arginine (R), aspartic acid (D) or glutamic acid (E),
$X_2$ is glutamine (Q), glutamic acid (E) or asparagine (N),
$X_3$ is proline (P),
$X_4$ is aspartic acid (D) or glutamic acid (E),
$Y_1$ is leucine (L), methionine (M) or isoleucine (I), and preferably leucine (L),
$Y_2$ is leucine (L),
$Y_3$ is valine (V), leucine (L) or methionine (M), and/or either n=m=a=c=0, or n=m=c=0 and a=1,
with the proviso that when $X_1$ is arginine (R) or lysine (K), then $Y_3$ is different from methionine (M).

More preferably, all the above conditions are met.

In a most preferred embodiment of this invention:
b=1 and $AA_2$ is glutamic acid (E),
$X_1$ is aspartic acid (D),
$X_2$ is glutamic acid (E),
$X_3$; is proline (P),
$X_4$ is glutamic acid (E),
$Y_1$ is leucine (L),
$Y_2$ is leucine (L),
$Y_3$ is methionine (M), and
either n=m=a=c=0, or n=m=c=0 and a=
More preferably, in the latter case, Ra=$CH_3$, $R_1$=H and $R_2$=CO—$(CH_2)_{14}$—$CH_3$.

In another most preferred embodiment:
b=2,
each of the AA2 groups is glutamic acid (E), and
Y1=Y2=leucine (L).

The peptides may be generated by conventional chemical synthesis or as fusion proteins in protein expression system of any species or by enzymatic synthesis (Kuliman et al., J. Biol. Chem., 1980) from constitutive amino acids or theirs derivatives. Peptides of this invention can still be obtained by biotechnology (use of a micro-organism, modified or not by genetic engineering); i.e., peptides according to this invention can also be obtained by fermentation of a strain of bacteria, modified or not, by genetic engineering to produce peptides of sequence previously mentioned and their fragments. Peptides of this invention can also be obtained from natural proteins; i.e. by protein extraction of animal or vegetable origin, followed by controlled hydrolysis which releases the peptide fragments of average size and of small size, provided that the released elements contain at least the sequence included in Formula (I). It is possible, but not necessary, to extract either the relevant proteins and then to hydrolyze them, or to initially carry out the hydrolysis on raw extract and then to purify the peptide fragments. Other more simple or more complex processes can be considered by the skilled in the art of synthesis, extraction and purification of proteins and peptides. Thus, the peptide compounds of this invention may be of natural or synthetic origin. Preferably, the peptide compounds of this invention are obtained by chemical synthesis.

The present invention also pertains to a cosmetic or dermatological composition comprising at least one peptide compound as described above, or a mixture thereof, in a physiologically acceptable medium.

By "physiologically acceptable medium", it is intended to designate a carrier adapted for topical application onto skin. This medium is preferably cosmetically acceptable, i.e. it does not generate any substantial irritation, redness or heating when applied onto human skin.

DETAILED DESCRIPTION OF THE INVENTION

The amount of compounds of Formula (I) included in this composition may be any sufficient amount to provide the required whitening effect. For instance, these compounds may represent from 0.001 to 20% by weight, and more preferably from 0.01 to 10% by weight, and still more preferably from 0.1 to 5% by weight, relative to the total weight of the composition.

This composition can be solid, semi-solid or liquid. It may be for instance in the form of a powder, ointment, paste, cream, fluid, milky lotion, cosmetic water, lotion, serum, gel, foam, facial mask such as a sheet mask, watery or anhydrous stick, and the like. Preferably, this composition includes water. More preferably, it is in the form of a gel or of an oil-in-water or water-in-oil, for instance water-in-silicon, emulsion. Alternatively, it may be in the form of a multiple emulsion, a micro-emulsion, nano-emulsion or a dispersion.

The composition according to this invention may contain various additives, such as at least one compound chosen from:
- oils, which can be chosen, in particular, from: volatile or non-volatile, linear or cyclic silicone oils, such as dimethylpolysiloxanes (dimethicones), polyalkylcyclosiloxanes (cyclomethicones) and polyalkylphenylsiloxanes (phenyldimethicones); synthetic oils such as fluorinated oils, alkyl benzoates and branched hydrocarbons such as polybutene; vegetable oils and, in particular, soybean or jojoba oil; and mineral oils such as paraffin oil;
- waxes, such as ozokerite, polyethylene wax, beeswax or carnauba wax;
- silicone elastomers obtained, in particular, by reacting, in the presence of a catalyst, a polysiloxane having at least one reactive group (hydrogen or vinyl, in particular) and carrying at least one end and/or side alkyl (in particular methyl) or phenyl group, with an organosilicon such as an organohydrogenpolysiloxane;
- surfactants, preferably emulsifiers, whether non-ionic, anionic, cationic or amphoteric, and, in particular, esters of fatty acids and polyols, such as esters of fatty acids and glycerol, esters of fatty acids and sorbitan, esters of fatty acids and polyethylene glycol; esters of fatty acids and sucrose; esters of fatty alcohols and polyethylene glycol; alkylpoyglucosides; modified polysiloxanes polyethers; betaine and its derivatives; polyquaterniums; sulphate salts of ethoxylated fatty alcohols; sulfosuccinates; sarcosinates; alkyl- and dialkylphosphates and their salts; and soaps of fatty acids;
- cosurfactants such as linear fatty alcohols and, in particular, hexadecyl and stearyl alcohols;
- thickeners and/or gelling agents, and, in particular, hydrophilic or amphiphilic, crosslinked or non-crosslinked homo- and copolymers of acrylamidoethylpropane sulfonic acid (AMPS) and/or of acrylamide and/or of acrylic acid and/or of salts or esters of acrylic acid; xanthan or guar gum; cellulose derivatives; and silicone gums (dimethiconol);
- humectants, such as polyols, including gylcerin, propylene glycol and sugars, and mucopolysaccharides such as hyaluronic acid and its salts and esters;
- agents for facilitating percutaneous absorption, such as alcohols, fatty alcohols and fatty acids and their ester or ether derivatives, pyrrolidones, terpenes, essential oils and α-hydroxy acids;
- colorants;
- preservatives;
- optical modifiers or soft focus agents such as non-colored and colored, organic and inorganic materials. Among the materials which may be used are included: organic pigments, inorganic pigments, polymers and fillers. The particles that can be present in the present invention can be natural, synthetic, or semi-synthetic. These optical modifiers can be platelet-shaped, spherical, elongated or needle-shaped, or irregularly shaped, surface coated or uncoated, porous or non-porous, charged or uncharged. Such particles useful herein include but are not limited to mica, zeolite, kaolin, silica, boron nitride, lauroyl lysine, nylon, polyethylene, talc, styrene, polypropylene, polystyrene, ethylene/acrylic acid copolymer, aluminum oxide, silicone resin, calcium carbonate, cellulose acetate, PTFE, polymethyl methacrylate, starch. The particles can be interference pigments with pearl gloss such as those supplied by EMD Chemicals, Inc. under the trade name TIMIRON (Registered trademark), COLORONA (Registered trademark) and supplied by Engelhard Co. under the trade name FLAMENCO (Registered trademark), TIMICA (Registered trademark). The particles can also be a composite powder such as a talc/titanium dioxide/alumina/silica composite powder, for example those sold under the name Coverleaf AR-(Registered trademark) by the company Catalyst & Chemicals. Of course, the formulation can contain a mixture of optical modifiers, each containing characteristics of a specific visual benefit, to create a combination of visual effects;
- sequestering agents such as the salts of EDTA;
- fragrances;
- and their mixtures, without this list being limiting.

Examples of such additives and others are cited in particular in the CTFA Dictionary (International Cosmetic Ingredient Dictionary and Handbook published by the Cosmetic, Toiletry and Fragrance Association, 10$^{th}$ Edition, 2004).

Furthermore, the topical composition of the present invention may suitably contain various active agents which may be chosen from the group consisting of:

antioxidants, such as ascorbic acid and its derivatives, including ascorbyl palmitate, ascorbyl tetraisopalmitate, ascorbyl glucoside, magnesium ascorbyl phosphate, sodium ascorbyl phosphate and ascorbyl sorbate; tocopherol and its derivatives, such as tocopheryl acetate, tocopheryl sorbate and others esters of tocopherol; BHT and BHA; and plant extracts, for instance from *Chondrus cripsus, Rhodiola, Thermus thermophilus*, mate leaf, oak wood, kayu rapet bark, sakura leaves and ylang ylang leaves;

anti-ageing agents, such as acyl aminoacids (for instance Maxilip, Matrixyl 3000 or Biopeptide CL from SEDERMA or Sepilift from SEPPIC), *Pisum sativum* extracts, hydrolyzed soy proteins, methylsilanol derivatives such as methylsilanol mannuronate, hydrolyzed *cucurbita* pepo seedcake, *Scenedesmus* extract;

anti-pollution agents such as Moring a pterygosperma seed extracts;

keratolytic agents, such as α-hydroxyacids (for instance, glycolic, lactic, citric, malic, mandelic or tartaric acid) and β-hydroxyacids (for instance, salicylic acid), and their esters, including $C_{12-13}$ alkyl lactate, and plant extracts containing these hydroxyacids, such as *Hibiscus sabdriffa* extracts;

astringents such as *hamamelis* extracts;

moisturizers, including plant extracts such as *Castanea sativa* extracts, hydrolyzed hazelnut proteins, *Polyanthes tuberosa* polysaccharides, *Argania spinosa* kernel oil and an extract of pearl containing conchiolin that is sold especially by the company Maruzen (Japan) under the trade name Pearl Extract®; homo- and copolymers of 2-metharyloyloxyethylphosphorylcholine, such as Lipidure HM and Lipidure PBM from NOF; saccharides such as glucose, fructose, mannose or trehalose; glycosaminoglycanes and their derivatives such as hyaluronic acid, sodium hyaluronate and acetylated hyaluronic acid; panthenol; allantoin; aloe vera; free amino acids and their derivatives; glucosamine; citric acid; urea and its derivatives and ceramides;

emollients such as glyceryl polymethacrylate; anti-inflammatory agents, such as bisabolol, allantoin, tranexamic acid, zinc oxide, sulfur oxide and its derivatives, chondroitin sulfate, glycyrrhizinic acid and its derivatives such as glycyrrhizinates;

and their mixtures.

The topical composition can also include organic and/or inorganic sunscreens. Among organic sunscreens, mention can be made of dibenzoylmethane derivatives such as butyl methoxydibenzoylmethane (Parsol 1789 from HOFFMANN LA ROCHE), cinnamic acid derivatives such as ethylhexyl methoxycinnamate (Parsol MCX from HOFFMANN LA ROCHE), salicylates, para-aminobenzoic acids, β-β'-diphenylacrylate derivatives, benzophenone derivatives, benzylidenecamphor derivatives such as terephtalylidene dicamphor sulphonic acid, phenylbenzimidazole derivatives, triazine derivatives, phenylbenzotriazole derivatives, anthranilic derivatives, all of which may be coated or encapsulated. Among inorganic photoprotective agents, mention can be made of pigments or alternatively nanopigments formed from coated or uncoated metal oxides, such as, for example, titanium oxide, iron oxide, zinc oxide, zirconium oxide or cerium oxide nanopigments; which are all CV photoprotective agents well known per se.

In addition, the pH of the topical composition of the present invention is preferably in the range from 4 to 8, and preferably from 4.5 to 7.

The cosmetic compositions according to the present invention may composition according to the invention contains at least one whitening agent able to block the synthesis of structural proteins involved in the mechanism of melanogenesis (stage I) such as the melanocyte-specific glycoprotein Pmel17. Such an active agent may be the tranexamic cetyl ester (trans-4(aminomethyl)cyclohexanecarboxylic acid hexadecyl ester hydrochloride) sold by Nikko Chemicals (Japan) or the ferulic acid Cytovector (water, glycol, lecithin, ferulic acid, hydroxyethylcellulose) sold by BASF under the trade name Cytovector®.

As a variant or in addition, the composition according to the invention may comprise a whitening agent having an inhibition effect on melanin synthesis and/or an inhibition effect on MITF expression and/or an anti-tyrosinase activity and/or an inhibition effect on endothelin-1 synthesis, such as a licorice extract (*glycyrrhiza glabra* extract), which is sold especially by the company Maruzen under the trade name Licorice Extract®.

As a variant or in addition, the composition according to the invention may comprise a whitening agent having an antioxidant effect as well, such as vitamin C compounds, including ascorbate salts, ascorbyl esters of fatty acids or of sorbic acid, and other ascorbic acid derivatives, for example, ascorbyl phosphates, such as magnesium ascorbyl phosphate and sodium ascorbyl phosphate, or saccharide esters of ascorbic acid, which include for instance ascorbyl-2-glucoside, 2-O— alpha-D-glucopyranosyl L-ascorbate, or 6-O— beta-D-galactopyranosyl L-ascorbate. An active agent of this type is sold especially by the company DKSH under the trade name Ascorbyl Glucoside®.

Other whitening agents may be included in the compositions according to this invention. Mention can be made of depigmenting agents such as plant extracts including *Narcissus tazetta* extracts; arbutin; kojic acid; ellagic acid; cysteine; 4-thioresorcin; resorcinol or rucinol or their derivatives; glycyrrhizinic acid and hydroquinone-beta-glucoside.

These compositions according to this invention may be used for depigmenting human skin in case of irregular pigmentation pattern due to acquired hyperpigmentation such as melasma (chloasma); postinflammatory melanoderma; solar lentigo; age spots (lentigo senile); pigmentation spots that appear on the skin upon sun exposure often in conjunction with drugs such as birth control pill or other hormonal medication, or following the application of a perfume, or during pregnancy; discoloration due to chemical peels and dermabrasion, pre- and post-laser resurfacing, or pre- and post-laser hair removal; pigmented keratosis or hypopigmentation after traumas (scars). Moreover they may also be used for lightening/brightening the complexion or forms of hyperpigmentation and hypopigmentation mentioned above.

The present invention thus also pertains to a cosmetic method for whitening, bleaching or lightening human skin, comprising topically applying onto human skin a cosmetic composition as described above.

It also relates to the use of the above composition for manufacturing a dermatological preparation intended to depigment human skin.

The skin areas on which the above process and use may be carried out may be any region of human skin preferably excluding the scalp, such as facial skin, breast skin, hand and arm skin or leg skin.

This invention will be better understood by reference to the following non-limiting Examples, taken in combination with the attached drawings in which:

EXAMPLES

The following examples further illustrate embodiments within the scope of the present invention. The examples are given solely for the purpose of illustration and are not to be construed as limitations of the present invention, as many variations thereof are possible without departing from the scope of the invention.

Example 1

Binding Test—Study of the Interactions of the Compounds According to this Invention with AP-2 and AP-3 Adaptor Complexes Synthesis:

Five peptide compounds in accordance with this invention were synthesized using amino acids protected with Fmoc [(N-(9-fluorenyl)methoxycarbonyl) and activated with benzotriazol-1-yl-oxytripyrrolidinophosphonium hexafluorophosphate and a peptide synthesizer. After cleavage from the resin and the protecting groups, peptides were purified by reverse phase HPLC using Delta Pac C-18 columns (Millipore) and an elution from 0-50% acetonitrile in 0.1% trifluoroacetic, water for 50 min. Purity of all peptides were 90% or better and was confirmed by HPLC, UV spectrometry, and mass spectrometry. All peptides were freeze dried and stored at −20° C. until use. Prior to biosensor experiments, all peptides were dissolved in HPLC-pure $H_2O$ to a stock concentration of 5 mM. Aliquots of this stock were frozen to avoid repeated freeze/thawing.

The compounds thus made consisted in the following peptide sequences:

| | |
|---|---|
| Compound 1: | DERQPLLVE |
| Compound 2: | EERQPMLLD |
| Compound 3: | AEDEPLLME |
| Compound 4: | AEDEPLLVD |
| Compound 5: | MVEENPILME |

None of these peptides is found in any known human protein. These compounds were tested for their ability to block the binding of adaptor complexes such as AP-2 and AP-3, which are key components in the melanogenesis process, to the human tyrosinase tail.

Test Protocol:

It is well established that adaptors such as AP-2 and AP-3 bind sorting signal containing peptides. Among them, the tyrosine-based signal of TGN38 is the most efficient AP-2 binding sequence known so far, while the same type of signal from Lamp-1 binds AP-1 and AP-3 and thus serves as a control for AP-3 binding in our experiments.

Human tyrosinase also contains tyrosine residues in its cytoplasmic tail sequence, however they are not relevant with respect to adaptor binding. Instead, the tail contains a dileucine-based sorting signal that is bound by adaptors such as AP-2 and AP-3.

Binding between adaptors and the tyrosinase tail peptide was recorded in real-time using a BIAcore 3000 biosensor (GEHealthcare) based on surface plasmon resonance. The tyrosinase tail peptide (sequence: -CRHKRKQLPEEKQ-PLLMEKEDYHSLYQSHL) (SEQ ID NO: 6) was immobilized on the surface of a CM5 sensor surface using thiol coupling and resulting in the immobilization of ≦300 RU of peptide. In brief, the CM5 surface was activated with EDC/NHS for 2 min at a flow-rate of 10 μl/min, followed by modification with PDEA for another 2 min. Subsequently, peptide was injected at a flow-rate of 5 μl/min for 1 min at a concentration of 5 μg/ml in 10 mM sodium acetate pH 4.5. The flow-rate was then adjusted to 20 μl/min and remaining active groups were blocked by injection of 50 mM cysteine, 1M NaCl. Following peptide immobilization, the surface was washed with buffer A (50 mM Tris pH 8.0, 250 mM NaCl, 0.005% Tween-20) at a flow rate of 30 μl/min. Purified adaptors were then injected at concentrations ranging from 100-1000 nM in buffer A for 2 min followed by dissociation for 2 min. The surface was regenerated by 2 pulse injection of 20 sec with 50 mM NaOH and 10 mM NaOH, 0.5% SDS. As controls for the sequence specific binding of the AP-2 and AP-3 adaptors, the tyrosine-based sorting signal peptides of TGN 38 (sequence-CRPKASDYQRL) (SEQ ID NO: 7) and Lamp-1 (sequence-CRKRSHAGYQTI) (SEQ ID NO: 8) were immobilized to the sensor surface exactly as described for the tyrosinase peptide.

For competition experiments, 200 nM adaptors were incubated with a 10-1000 fold molar excess of one of the 5 compound peptides for 10 min prior to injection. For comparison of adaptor binding to the immobilized tyrosinase tail, the RU values at the end of the injection (association period) and after the dissociation period were evaluated.

Results:

The results of these experiments are shown on the attached drawings.

Figure 1:
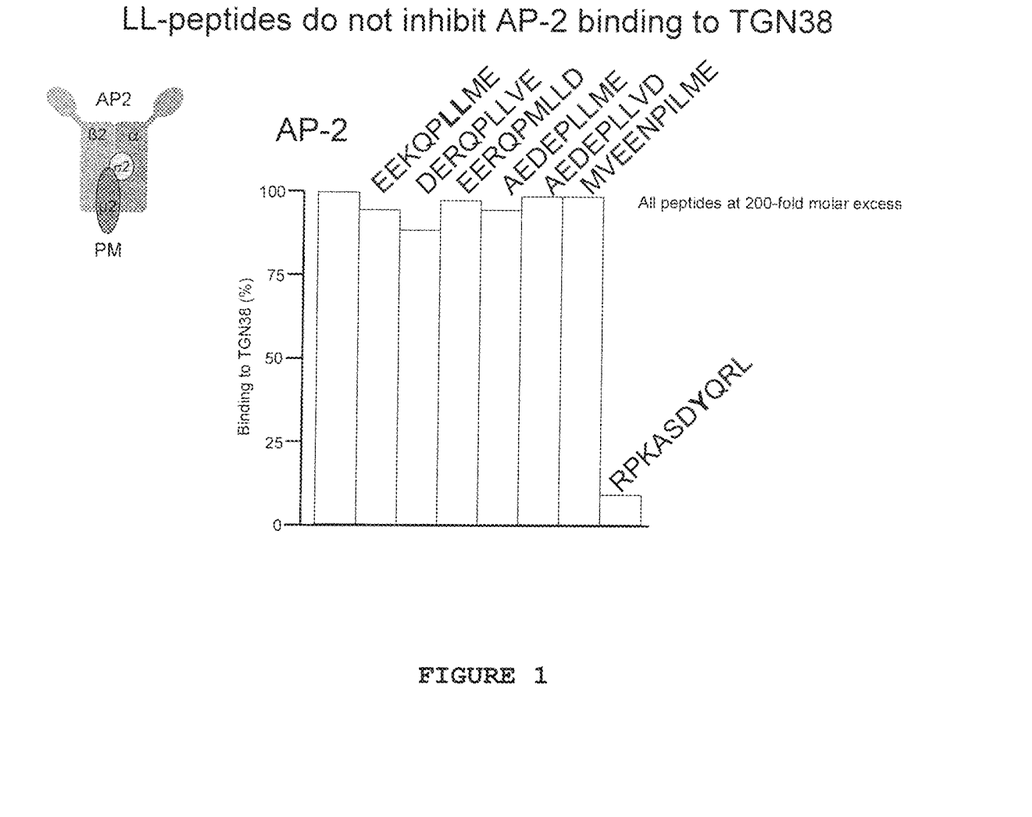
FIG. 1 is a histogram showing the inhibiting effect of various compounds of this invention on the binding of AP-2 to the tyrosine-based signal containing TGN38 peptide.

As illustrated in FIG. 1, the five compounds of this invention did not significantly inhibit the binding of AP-2 to TGN38, compared to RPKASDYQRL (SEQ ID NO: 9) which was used as a positive control since this peptide is known to bind to the μ2 chain of the AP-2 heterotetramer. It can thus be derived that the test compounds do not bind to the μ2 chain of AP-2.

Figure 2:
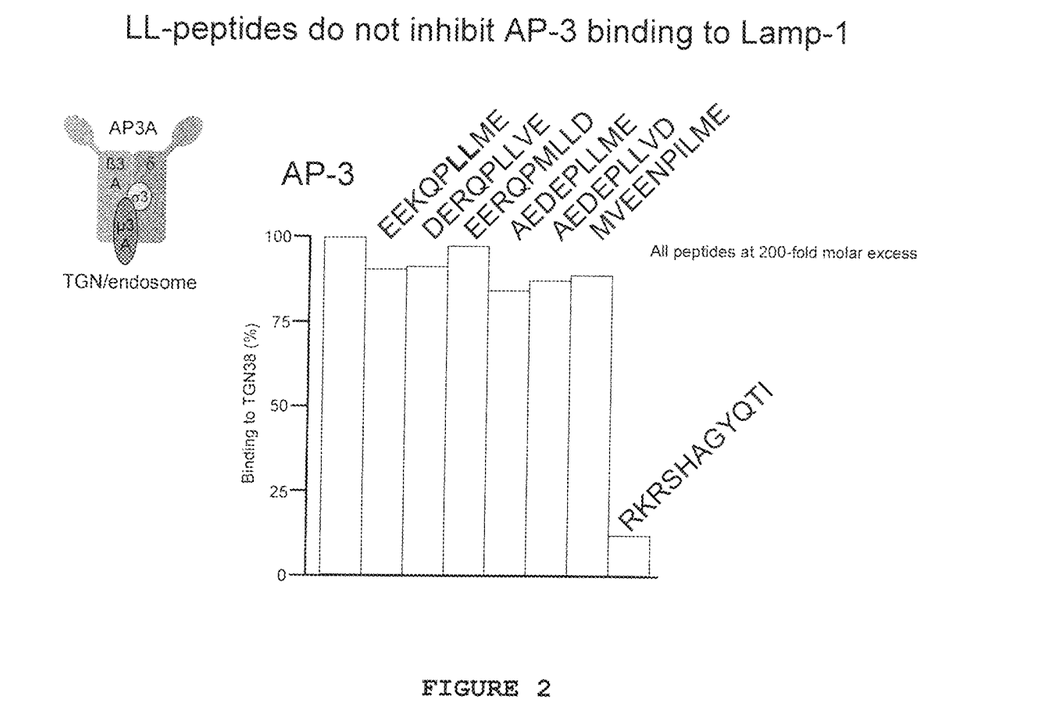
FIG. 2 is a histogram showing the inhibiting effect of various compounds of this invention on the binding of AP-3 to the tyrosine-based signal containing Lamp-1 peptide.

Moreover, as illustrated in FIG. 2, the five compounds of this invention did not significantly inhibit the binding of AP-3 to Lamp-1, compared to RKRSHAGYQTI (SEQ ID NO: 10) which was used as a positive control since this peptide is known to bind to the μ3 chain of the AP-3 heterotetramer. It can thus be derived that the test compounds do not bind to the μ3 chain of AP-3.

Example 2

Binding Test—Study of the Inhibiting Effect of the Compounds According to this Invention on Tyrosinase Binding to AP-2 and AP-3

A test similar to that described in Example 1 was conducted to determine the effect of the five compounds synthesized in Example 1 on the binding of tyrosinase to AP-2 and AP-3. The molar amount of adaptor and soluble peptides used for inhibition were exactly the same as outlined in Example 1.

The same control sequences were used as those used in Example 1 as negative controls since it is known that tyrosinase does not bind to the µ2 and µ3 chains of AP-2 and AP-3, respectively. Moreover, EEKQPLLME (SEQ ID NO: 11) was used as a positive control, since this sequence harbors the part of human tyrosinase that is known to bind to AP-2 and AP-3.

Figure 3:
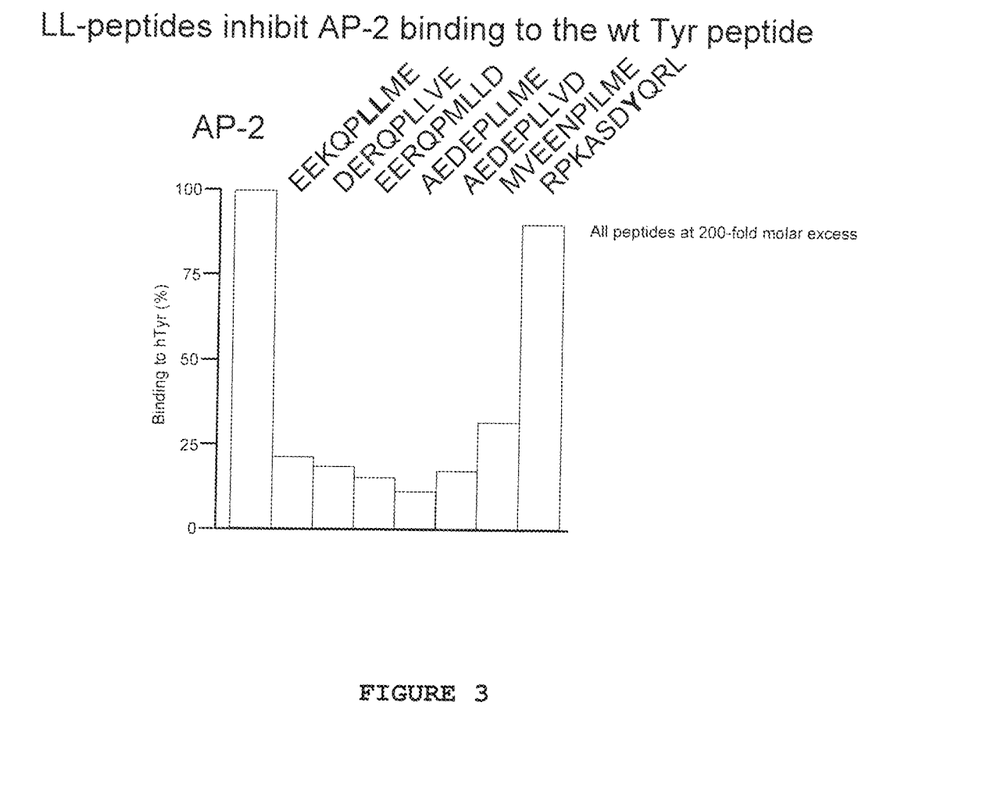
FIG. 3 is a histogram showing the inhibiting effect of various compounds of this invention on the binding of AP-2 to the dileucine-based sorting signal containing tyrosinase.

As can be seen in FIG. 3, the five compounds of this invention drastically inhibited the binding of AP-2 to tyrosinase with compound 4 being the most active.

Figure 4:
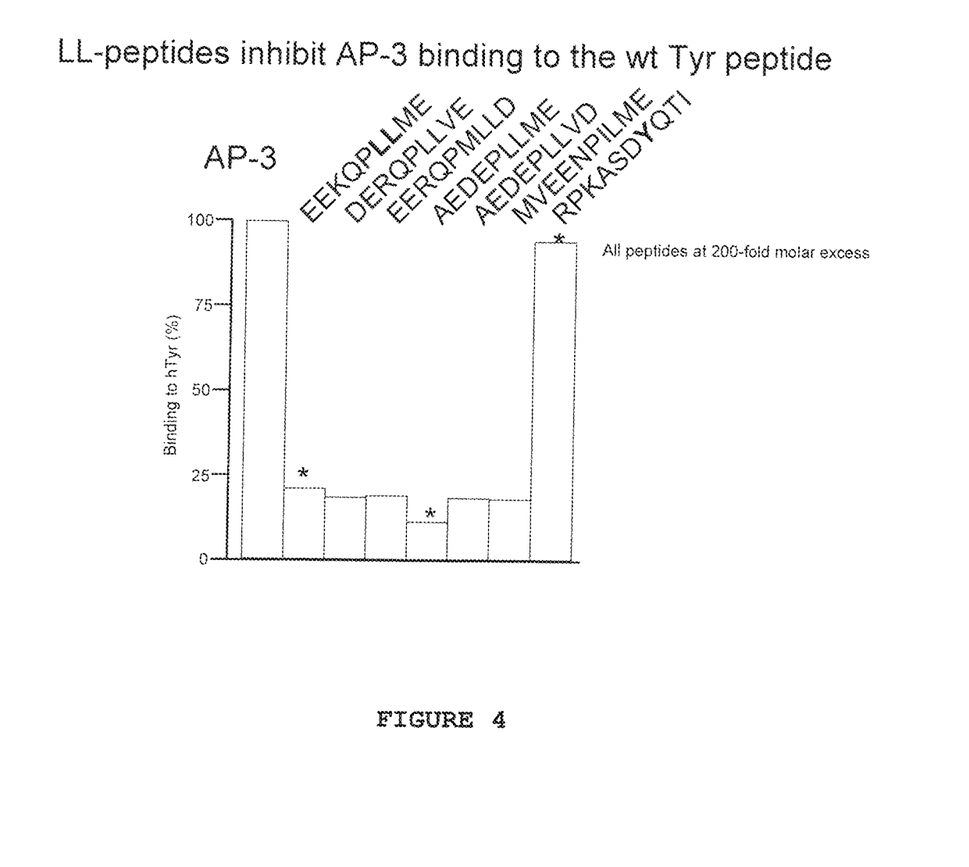
FIG. 4 is a histogram showing the inhibiting effect of various compounds of this invention on the binding of AP-3 to the dileucine-based sorting signal containing tyrosinase.

Moreover, as shown in FIG. 4, these compounds also very efficiently inhibited the binding of AP-3 to tyrosinase, with compound 4 again being the most active.

These examples thus demonstrate that the compounds according to this invention effectively block the binding of AP-2 and AP-3 to tyrosinase. It is thus believed that they will block the correct intracellular sorting of tyrosinase to melanosomes and thus melanin synthesis.

Example 3

Study of the Melanocyte Intracellular Penetration of the Peptide According to this Invention Test Protocol:

B16 melanoma cells were cultured at 37° C. and 5% of $CO_2$ in microplates with 96 wells in the presence of DMEM (Invitrogen, reference 11880028) containing 1 g/l of glucose without phenol red supplemented by 3 g/l of glucose (Sigma, reference G7021), 2 mM of L-glutamine, 50 UI/ml of penicillin, 50 µg/ml of streptavidin (Invitrogen, reference 15070063) and 10% of fetal veal serum (Invitrogen, 10270098). After 24 h, the culture medium is replaced by a DMEM medium containing or not (control) a stable derivative of α-MSH, i.e. NDP-MSH (NLE-4-D-PHE-7-A Melanocytes Stimulating Hormone, Sigma, reference M-8764) and containing or not the peptide (compound 3 of example 1 or its N-palmitoyl derivative) according to the invention. Each peptide was tested with and without lipofectamine, (Invitrogen, reference 1538-100), an agent used to facilitate the peptide penetration. The melanocytes were then incubated for 72 hours at 37° C. and 5% of $CO_2$.

At the end of the incubation period, the medium was eliminated and cells were rinsed with a solution of PBS (phosphate buffer saline). The penetration of each peptide was analyzed by microscopy (In Cell Analyser® 100, GE Healthcare) with the objective ×20 or by Flux Cytometry after unsticking of cells by enzymatic treatment with trypsine (Flux FACSarray, Becton Dickinson).

Results:

The following table 1 illustrates the measurement of the penetration of the peptide+FITC (fluoresceine isothiocyanate) in B16 melanocytes at different peptide concentrations (4, 20, 100 and 500 µg/ml).

TABLE 1

| Control without lipofectamine | Compound 3 according to Example 1 without lipofectamine (% control) | | | |
|---|---|---|---|---|
| (% control) | 4 µg/ml | 20 µg/ml | 100 µg/ml | 500 µg/ml |
| 100% | ns * | 263 | 533 | 1640 |
| Control with lipofectamine | Compound 3 according to Example 1 with lipofectamine (% control) | | | |
| lipofectamine | 4 µg/ml | 20 µg/ml | 100 µg/ml | 500 µg/ml |
| 109 | 166 | 338 | 1097 | 4265 |

TABLE 1-continued

| Control without lipofectamine | N-palmitoyl derivatives of compound 3 according to Example 1 without lipofectamine (% control) | | | |
|---|---|---|---|---|
| (% control) | 4 µg/ml | 20 µg/ml | 100 µg/ml | 500 µg/ml |
| 100 | 276 | 364 | 1486 | 982 |
| Control with lipofectamine | N-palmitoyl derivatives of compound 3 according to Example 1 with lipofectamine (% control) | | | |
| (% control) | 4 µg/ml | 20 µg/ml | 100 µg/ml | 500 µg/ml |
| 120 | 765 | 1495 | 1331 | 7726 |

\* ns: $p > 0.05$, not significant

The observation in fluorescence microscopy clearly demonstrates that peptides penetrate into cells and that this penetration increases with the addition of lipofectamine. These results were confirmed by flux cytometry, which showed that the intensity of fluorescence depends directly on the peptide concentration.

Example 4

Effect of the N-Palmitoyl Derivative of Compound 3 of Example 1 on Melanogenesis Test Protocol:

The protocol used is the same as in example 3. The melanocytes were incubated for 96 hours at 37° C. and 5% of $CO_2$. Kojic acid was used as a positive control.

At the end of the incubation period, the quantity of melanine was evaluated by measuring the absorption at 405 nm for each sample.

Results:

The following table 2 illustrates the effect on the synthesis of melanine of the N-palmitoyl derivative of compound 3 of example 1 at 0.5; 1; 2.5; 5 and 10 µg/ml.

TABLE 2

| Control without lipofectamine, | N-palmitoyl derivative of compound 3 of example 1 with out lipofectamine, with NDP-MSH (% of inhibition) | | | | |
|---|---|---|---|---|---|
| with NDP-MSH (% of inhibition) | 0.5 µg/ml | 1 µg/ml | 2.5 µg/ml | 5 µg/ml | 10 µg/ml |
| 0 | ns * | 9 | 10 | 14 | 20 |
| Control | Kojic acid with NDP-MSH (% of inhibition) | | | | |
| with NDP-MSH (% of inhibition) | 6.9 µg/ml | 15.6 µg/ml | 36 µg/ml | 80 µg/ml | |
| 0 | −13 | −7 | 33 | 75 | |

\* ns: $p > 0.05$, not significant

The presence of NDP-MSH sharply inferred the melanogenesis. This induction of the synthesis of melanin was sharply inhibited by kojic acid tested between 36 and 80 µg/ml. These results validate the test.

The presence of lipofectamine did not modify the synthesis of melanin by B16 melanocytes incubated with NDP-MSH.

The treatment with the N-palmitoyl derivative of compound 3 of example 1, tested between 1 and 10 µg/ml, in the absence of lipofectamine, allowed to inhibit sharply the melanogenesis boosted by the NDP-MSH (from 9 to 20% of inhibition). This inhibition increased with the presence of lipofectamine (from 5 to 29% of inhibition between 1 to 10 µg/ml).

Thus, this study confirms that peptides according to the invention, such as the N-palmitoyl derivative of compound 3 of example 1, inhibit the synthesis of melanine by the melanocytes.

Example 5

Cosmetic Compositions

The compositions given hereafter may be prepared by conventional methods from the following components. The contents are expressed by weight relative to the total weight of the composition.

Formula 5.1: Water in oil formula

| INCI NAME | QUANTITY |
| --- | --- |
| Ethylhexyl palmitate | 14.00 |
| Propylparaben | 0.30 |
| PEG-30 dipolyhydroxystearate | 3.00 |
| Silica dimethyl silylate | 2.00 |
| Hydrogenated polyisobutene | 31.49 |
| Ethylene/propylene/styrene copolymer | 2.62 |
| Butylene/ethylene/styrene copolymer | 0.88 |
| BHT | 0.01 |
| Water | 42.10 |
| Sodium chloride | 0.80 |
| Tetrasodium EDTA | 0.05 |
| Glycerin | 2.00 |
| Methylparaben | 0.30 |
| Xanthan gum | 0.35 |
| Peptide according to the invention - Compound 3 | 0.10 |

Formula 5.2: Serum

| INCI NAME | QUANTITY |
| --- | --- |
| Water | 85.19 |
| Tetrasodium EDTA | 0.05 |
| Polyethyleneglycol | 5.00 |
| Acrylates/$C_{10-30}$ alkyl acrylate crosspolymer | 0.35 |
| Ammonium acryloyldimethyltaurate/VP copolymer | 0.30 |
| Glycerin | 4.43 |
| PEG-8 | 1.00 |
| Sodium polyacrylate | 0.04 |
| Caprylyl glycol | 0.15 |
| PEG-11 methyl ether dimethicone | 3.00 |
| Propylene glycol | 0.01 |
| Propylparaben | 0.01 |
| Methylparaben | 0.31 |
| Sodium hydroxide | 0.06 |
| Peptide according to the invention - N-palmitoyl derivative of Compound 3 | 0.10 |

Formula 5.3: Gel-cream formula

| INCI NAME | QUANTITY |
| --- | --- |
| Water | 75.36 |
| Tetrasodium EDTA | 0.05 |
| Glycerin | 7.26 |
| Ammonium acryloyldimethyltaurate/VP copolymer | 0.80 |
| Acrylates/$C_{10-30}$ alkyl acrylate crosspolymer | 0.15 |
| Methylparaben | 0.30 |
| Cyclomethicone | 8.05 |
| Polysorbate-20 | 0.05 |
| Isononyl isonanoate | 3.00 |
| Dimethicone | 2.00 |
| Phenyl trimethicone | 2.00 |
| Tocopheryl acetate | 0.50 |
| Polyacryl amide | 0.12 |
| Hydrogenated polyisobutene | 0.05 |
| Laureth-7 | 0.02 |
| Hydroxyethyl acrylate/sodium acryloyldimethyl taurate copolymer | 0.09 |
| Squalane | 0.01 |
| Polysorbate 60 | 0.01 |
| Sorbitan isostearate | 0.02 |
| Sodium hydroxide | 0.02 |
| Peptide according to the invention - Compound 5 | 0.10 |

The invention claimed is:

1. A compound having the following formula (I):

(I)

wherein:

$R_1$, $R_2$, $R_3$ each independently represent:
H, a $C_2$-$C_{22}$ optionally hydroxylated and/or sulphured linear hydrocarbon group which may be saturated or unsaturated, a $C_3$-$C_{22}$ optionally hydroxylated and/or sulphured branched or cyclic hydrocarbon group which may be saturated or unsaturated, or a biotin group, wherein at least one of $R_1$ and $R_2$ may alternatively be a protective group or a blocking group;

Ra and Rb each independently represent:
H, a $C_1$-$C_4$ linear alkyl group, or a $C_3$-$C_4$ branched alkyl group, each alkyl group optionally being substituted by one or more substituents selected from the group consisting of: OH, SH, COOH, $CONH_2$, $NH_2$—S—$CH_3$, NH—C(NH)—$NH_2$ or by a cyclic or heterocyclic aromatic group;

$X_1$ is arginine (R), aspartic acid (D), or glutamic acid (E);
$X_2$ is glutamine (Q), glutamic acid (E) or asparagine (N);
$X_3$ is proline (P);
$X_4$ is aspartic acid (D) or glutamic acid (E);
$Y_1$ is leucine (L), methionine (M) or isoleucine (I);
$Y_2$ is leucine (L);
$Y_3$ is valine (V), leucine (L) or methionine (M);
$AA_1$ is an amino acid;
$AA_2$ is glutamic acid (E);
m=1; b=1; and each of a and c=0 or 1,
wherein each amino acid may independently be in a L, D or DL configuration, with the proviso that when $X_1$ is arginine (R), then $Y_3$ is not methionine (M).

2. The compound according to claim 1, wherein at least one of $R_1$ and $R_2$ is an alkyl carbonyl group having from 6 to 20 carbon atoms, optionally hydroxylated and/or sulphured.

3. The compound according to claim 2, wherein at least one of the $R_1$ and $R_2$ groups is a palmitoyl group.

4. The compound according to claim 1, wherein:
$X_1$ is aspartic acid (D),
$X_2$ is glutamic acid (E),
$X_3$ is proline (P),
$X_4$ is glutamic acid (E),
$Y_1$ is leucine (L),
$Y_2$ is leucine (L), and
$Y_3$ is methionine (M).

5. A cosmetic or dermatological composition comprising at least one peptide compound as described in claim 1, or a mixture thereof, in a physiologically acceptable medium.

6. A cosmetic or dermatological composition comprising at least one peptide compound as described in claim 4, or a mixture thereof, in a physiologically acceptable medium.

7. A cosmetic method for whitening, bleaching or lightening human skin, comprising topically applying onto human skin the cosmetic composition according to claim 5.

8. The compound according to claim 1, selected from the group consisting of:
 DERQPLLVE (SEQ ID NO: 1),
 EERQPMLLD (SEQ ID NO: 2),
 AEDEPLLME (SEQ ID NO: 3), and
 AEDEPLLVD (SEQ ID NO: 4).

* * * * *